United States Patent [19]

Gratzner

[11] Patent Number: 4,529,700
[45] Date of Patent: Jul. 16, 1985

[54] HYBRIDOMA CELLS SECRETING A MONOCLONAL ANTIBODY SPECIFIC FOR 5-BROMO AND 5-IODOEOXYURIDINE AND REAGENTS FOR MEASURING CELLULAR PROLIFERATION

[75] Inventor: Howard G. Gratzner, Miami, Fla.

[73] Assignee: University of Miami, Miami, Fla.

[21] Appl. No.: 409,856

[22] Filed: Aug. 20, 1982

[51] Int. Cl.³ .................. C12N 5/00; C12N 15/00; C12Q 1/68; G01N 33/54
[52] U.S. Cl. .................................. 435/240; 435/6; 435/7; 435/172.2; 435/948; 436/548; 935/103; 935/110
[58] Field of Search .......... 435/6, 7, 240, 241, 435/172, 948, 172.2; 436/540, 548; 935/103, 95, 110, 108

[56] References Cited

U.S. PATENT DOCUMENTS 4,172,124 10/1979 Koprowski et al. ............. 435/240
4,196,265 4/1980 Koprowski et al. ............. 435/240
4,284,412 8/1981 Hansen et al. .................. 436/548

OTHER PUBLICATIONS

Vossius, *Banbury Report* 10, Patenting of Life Forms, Plant et al Ed., Cold Spring Harbor Laboratory, 187–190, (1982).
Shulman et al, Nature, 276: 269–270, (1978).
Gratzner et al, Chemical Abstracts, 84:71158c, 192, (1976).
Gratzner et al, Chemical Abstracts, 89:142829p, 272, (1978).
Gratzner et al, Chemical Abstracts, 83:189988f, 190, (1975).
Gratzner et al, Chemical Abstracts, 98:85553d, 245, (1983).
Hyberlines, vol. I, No. 5, Dec. 1980, p. 5, "Lab Notes", righthand col.
Gratzner et al: Exp. Cell Res. 95, (1975), 88–94, "The Use of Antibody Specific for Bromodeoxyuridine for the Immunofluorescent . . . ".
Gratner et al: "Immunochemical Studies of 5--Bromodeoxyuridine", Res. Com. in Chem. Path. and Phar., vol. 20, No. 3, Jun. 1978, p. 539.
Gratzner et al: "Deoxyribonucleic Acid Replication in Single . . . ", J. Histochem. and Cytochem., vol. 24, No. 1, pp. 34–39, 1976.
Gratzner et al, "An Immunofluorescence Method for Monitoring DNA . . . ", Cytometry, vol. 1, No. 6, 1981, pp. 385–389.

*Primary Examiner*—Esther M. Kepplinger
*Attorney, Agent, or Firm*—Cushman, Darby & Cushman

[57] ABSTRACT

Cells synthesizing DNA are detected in a rapid, nonradioactive assay using the monoclonal antibody reagent secreted by the hybridoma produced in accordance with the present invention. The assay is used to study DNA repair in cells that have been exposed to various environmental toxins, chemotherapeutic agents, and the like. The monoclonal antibody secreted by the hybridoma is a valuable reagent for research and diagnosis.

1 Claim, 3 Drawing Figures

HYBRIDOMA CELLS SECRETING A MONOCLONAL ANTIBODY SPECIFIC FOR 5-BROMO AND 5-IODOEOXYURIDINE AND REAGENTS FOR MEASURING CELLULAR PROLIFERATION

This invention relates to materials used in a procedure for measuring DNA synthesis, and more specifically to the production in living cells of antibodies specific for 5-bromodeoxyuridine (BrdUrd) and iododeoxyuridine (IdUrd), and the production of monoclonal antibodies specific for those compounds by fused, hybrid cells. The hybridoma cells produce antibodies that are used as a pure reagent for measuring cellular proliferation. DNA synthesis is measured to determine if cells are replicating and to assess the response of cells to a drug substance, a hormone or the like.

BACKGROUND OF THE INVENTION

The detection of replicating cells is usually accomplished by demonstrating that [$^3$H]-thymidine, or other DNA precursor, is incorporated into DNA. This is detected by either autoradiography or scintillation counting, as described by Taylor, et al, Proc. Natl. Acad. Sci., U.S.A. 43:122 (1957) and R. Baserga and D. Malamud, Autoradiography: Technique and Application, Harper, N.Y. (1969).

The process of autoradiography involves overlaying a microscope slide having [$^3$H]-DNA incorporated on it with a photographic emulsion. The emulsion-bearing slide is stored for a time sufficient to expose the emulsion to particles emitted from the decaying tritium; this period usually takes several days and may last as long as several weeks. The slide is photographically developed revealing "fogging" of the emulsion caused by radiation issued from the decaying tritium. This radiation causes the silver grains in the emulsion to be visible over only those cells which have incorporated [$^3$H]-thymidine into their DNA. The proportion of DNA-synthesizing cells in the total population is then enumerated microscopically. Approximate quantitation of the amount of radioactive DNA synthesized per cell can be estimated by counting the silver grains overlying each cell.

Another method of measuring DNA synthesis involves the quantitation of isotopic incorporation of a DNA precursor, such as [$^3$H]-thymidine, [$^{14}$C]-thymidine, or [$^{125}$I] iododeoxyuridine, or one of the other nucleosides which are DNA precursors and are readily incorporated into DNA. The DNA of a number of cells is extracted and treated then counted in a liquid scintillation spectrometer.

While autoradiography is used to measure replication in individual cells, scintillation counting of the incorporated radioactivity is a "batch" process in which only the total amount of radioactivity is measured. Thus, the frequency of replicating cells in a population cannot be measured. It is also to be noted that both autoradiography and scintillation counting techniques require the use of radioisotopes; this contributes a radiation hazard, with attendant handling and disposal precautions.

The process of DNA synthesis can also be measured by the use of 5-iododeoxyuridine and 5-bromodeoxyuridine, both of which are chemical analogues of thymidine. Since these compounds appear to the cell as thymidine, they are usually incorporated into DNA in place of thymidine; see Hughes, et al, Fed. Proc. 23:640 (1964). Thus, the de novo synthesis of DNA can be monitored by measuring in some manner the incorporation of these base analogues by isotopic techniques ($^{125}$I-dUrd), as described above, or increased DNA density (Lark, et al, Biochim. Biophys. Acta, 76, 9-24 1963), as fluorescence quenching or enhancement of fluorescence of certain DNA-binding dyes, as described by Latt, Proc. Natl. Acad. Sci. (U.S.A.) 70:3395 (1973); and Swartzendruber, Exp. Cell. Res. 109:439 (1977).

Antibodies specific for BrdUrd and IdUrd were produced in rabbits by Sawicki, et al, Science 174:70 (1977). In this study rabbits were immunized with bovine serum albumin conjugates of 5-bromouracil, 5-iodobromouracil, and 6-methyladenosine which produced antibodies specific for the bases. These antibodies were used to detect immunochemically 5-bromouracil and 6-methyladenosine in denatured DNA. This type of antibody was applied to the detection of DNA replication in mammalian cells by immunocytochemical means, see Gratzner, et al, Exp. Cell Res. 95:88 (1975) and J. Histochem. Cytochem. 24:34 (1976); and by flow cytometry, Gratzner and Leif, Cytometry 1:385 (1981).

While antibodies raised in rabbits are useful, cross-reaction of the antibodies with thymidine limited the utility of the immunofluorescent technique, since it was difficult to absorb out all of the crossreacting species; accurate titrations were found to be necessary in order to obtain an optimal concentation of antibody which would react only with bromodeoxyuridine and not with thymidine. The monoclonal antibody of the present invention only reacts with bromodeoxyuridine or iododeoxyuridine; no crossreaction whatever has been observed with thymidine at any concentration of antibody tested. Thus, the monoclonal antibody has the advantage of not requiring titration and thus much greater signal to noise ratio (fluorescence intensity of BrdUrd-incorporated DNA:intensity of control).

The present invention relates to a process for producing in living cells antibodies specific for 5-bromodeoxyuridine and 5-iododeoxyuridine and more specifically to the production of monoclonal antibodies that are specific for those compounds from fused, hybrid cells.

The antibodies produced by such cells either in culture or in vivo can be used to detect cell proliferation in vivo or in vitro. The antibodies can also be used for the isolation of segments of DNA containing these bases or for the immunological detection of replicating DNA by fluorescence, bright field or by electron microscopy.

BRIEF DESCRIPTION OF THE DRAWINGS

FIGS. 2A and 2B are the results of flow cytometric analyses of BrdUrd-labelled WiL2 human lymphoblast cells. The data in FIG. 2A shows the cells incubated without BrdUrd while FIG. 2B shows the data obtained from cells that were incubated in 10 μm BrdUrd.

DESCRIPTION OF THE INVENTION

Figure 1:
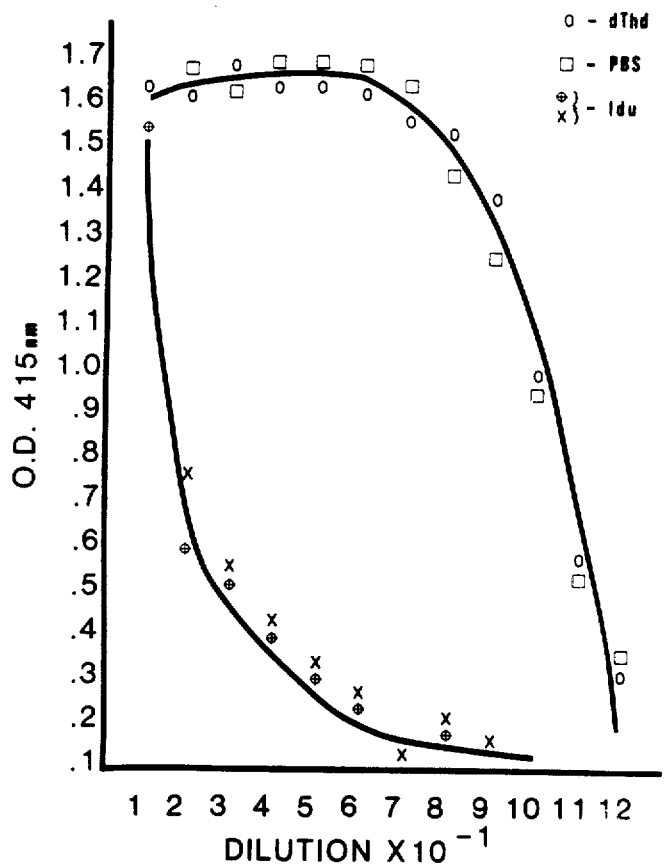
FIG. 1 is a graph depicting the specificity of the anti-BrdUrd/IdUrd antibody for iododeoxyuridine and non-reactivity towards thymidine as demonstrated by an enzyme-linked immunoabsorbant assay (ELISA), described in more detail below. In this graph dThd represents thymidine, PBS is phosphate buffered saline, and Idu is iododeoxyuridine.

In general the invention includes a process for producing anti-BrdUrd and anti-IdUrd antibodies by the fusion of antibody-producing cells taken from animals using a continuous cell line, then selecting a candidate hybrid cell, and thereafter producing and collecting the desired antibodies.

BRIEF DESCRIPTION OF THE INVENTION

This invention is the result of the fusion of murine plasmacytoma cells (SP 2/0) with cells from the spleen of a mouse immunized against the conjugate between 5-iodouridine and ovalbumin. Clones of the hybridoma cells from this fusion which secreted significant amounts of a single, specific type of antibody, namely an immunoglobulin specific for the base analogues 5-iodouridine and 5-bromouridine were selected and further cloned by limiting dilution and colony formation in agarose. Since these analogues can be incorporated into DNA in place of thymidine, their positive detection in cellular DNA will be an indication that the cells have synthesized their DNA and thus in the process of replication.

The monoclonal antibodies produced by the hybridoma cells can be recovered from the culture medium and employed as a pure reagent to detect the iodo- and/or bromodeoxyuridine in cells. The monoclonal antibody can either be directly "tagged" with a fluorescent molecule or enzyme, or indirectly detected by use of a second antibody or similar molecule which has been tagged. By immunofluorescence or enzyme linked immunoabsorbant assay (ELISA), the presence of bound antibody can be detected.

This method described is analogous to the detection of DNA synthesis by the use of the radiotracer, tritiated thymidine. However, no isotopes are employed and the immunological technique is quite rapid when compared to its counterpart method, autoradiography; detection can be made in several hours or less, in comparison to days to weeks with autoradiography.

Various end uses and applications for the products and techniques of the present invention are available. The invention also includes incorporating antibodies which are specific for base analogues into DNA for the purpose of detecting DNA synthesis and, in general, cell proliferation. These antibodies are also useful for monitoring the effects of chemotherapeutic modalities, such as the effect of radiation or drugs on tumor growth, by immunological means such as immunofluorescence or ELISA methods.

These antibodies are also useful in the immunological detection of transplantation incompatibility, for example in mixed lymphocyte culture (MLC), to detect histoincompatibilities.

The antibodies of the invention are also used for in situ detection of DNA synthesis by electron micrographic methods, immunofluroescence or enzyme-coupled antibody methods. These antibodies are particularly well adapted for flow cytometry or other automated cytometric techniques, for example as performed on slides, sometimes called image cytometry.

The novel antibodies of the invention are also useful in the characterization of chromosomes, as for replication of segments of the chromosomes, and/or as a means of identifying a particular chromosome, or of identifying a particular genetic syndrome which might be manifested by an alteration in chromosome replication.

The identification of toxic substances by techniques involving methods related to the use of anti-BrdUrd or other antibody to base analogues is also within the present invention. This also includes the use of the novel antibody to detect mutations or alterations in the DNA synthesis rate or alteration in kinetics of cells.

The detection of DNA sequences by hybridization with a BrdUrd-containing "probe" DNA, including immunofluoroescent labels for DNA probes, to detect viral genes to detect a specific viral infection, or cancer detection by DNA electrophoresis and in situ localization are also contemplated.

The isolation of DNA by affinity chromatography on antibody-coupled resins or other substances for the purpose of purifying specific, newly replicated DNA sequences is also possible as is the detection of DNA "repair" synthesis by using the monoclonal antibodies herein disclosed. Cytological detection of messenger DNA by the use of BrdUrd-containing probes is also within the ambit of this invention.

In this disclosure the following terms and abbreviations are used:

IdUrd = 5-iododeoxyuridine
BrdUrd = 5-bromodeoxyuridine
ELISA = enzyme linked immunoabsorbant assay
MLC = mixed lymphocyte culture
BrUrd = boromouridine
IUrd = iodouridine
PBS = phosphate buffered saline
HAT medium = hypoxanthine, thymidine and methotrexate medium
BSA = bovine serium albumin

DESCRIPTION OF THE PREFERRED EMBODIMENTS

Preparation of the Anti-BrdUrd Monoclonal Antibody

The conjugation of bromouridine (BrUrd) or iodouridine (IUrd) to a carrier macromolecule, typically ovalbumin, was performed as described in Erlanger and Beiser, Proc. Natl. Acad. Sci. 52:68–74 (1964) U.S.A. the disclosure of which is hereby incorporated by reference. In this procedure mice were immunized with two hundred µg of the conjugate injected peritoneally in an emulsion with an equal volume of Freund's complete adjuvant. Subsequent injections were made in incomplete adjuvant every two weeks, the final injection of IUrd-ovalbumin being made in saline into the tail vein 3 days prior to the fusion of the spleen cells. Fusion of spleen cells from the immunized mice with the continuous plasma-cytoma cell line SP2/O Ag 14, M. Shulman et al, Nature 276:269 (1978), was performed using polyethylene glycol (30%) in the method described by Gefter, et al, Somatic Cell Genetics, Vol. 3:231 (1977). Preparation of spleen cells and fusion has also been described by Koprowski, et al in U.S. Pat. Nos. 4,172,124 and 4,196,265 the disclosures of which are hereby incorporated by reference.

The cells from the spleen cell/cell line fusion were plated in four microculture plates (96-well each, COSTAR) in Dulbecco's Minimal Essential Medium (GIBCO) containing 15% fetal bovine serum. Twenty-four hours subsequent to the fusion and plating, medium containing hypoxanthine, thymidine and methotrexate (HAT Medium) is added to each well in order to select the hybrid cells. The incubation is then continued for about ten days.

Colonies are first visible after five or six days. Cells from wells containing colonies were passed into 24-well microculture plates and the media from these and the 96-well plates were assayed by an enzyme-linked immunoabsorbant assay (ELISA). The ELISA assay is similar to the assay presented by BRL Corporation in Hybrlines newsletter (BRL) 1:5 p. 5 (December 1980).

In the ELISA procedure polyvinyl chloride plates were coated with the hapten conjugated to a carrier different than the one used for immunization of the mice, such as iodouridine-BSA (bovine serum albumin) at a concentration of 500 ng per well, together with 19 μl per well of a carbodiimide, 1-ethyl-3(3-dimethylaminopropyl) carbodiimide, available commercially as EDAX from Biorad Corporation in sodium carbonate buffer. The plates are incubated overnight at 4° C. and then washed with PBS four times and treated with 0.1M NH$_4$Cl at room temperature for 30 minutes in order to bind the residual active groups. The wells of the microtiter plates are then washed with phosphate buffered saline (PBS) and stored in PBS containing 0.05% sodium azide at 4° C., until use.

The supernatants from the wells of the hybridoma fusion plates are added to the wells of the microtiter plates containing the IUrd-BSA (at a volume of 100 μl per well) and incubated at 4° C. for one hour. After washing the wells free of the supernatants from the hybridoma fusion, sheep or goat anti-mouse IgG coupled to β-galactosidase was added and the plates were then incubated for two hours at room temperature. The plates were washed again with a solution of phosphate buffered saline containing 0.5% Tween 20, 1.5 mM MgCl$_2$, 2 mM mercaptoethanol, and the β-galactosidase substrate added and the plates incubated for an additional hour. The β-galactosidase substrate consisted of p-nitrophenyl-galactoside diluted in 50 mM phosphate buffer, pH 7.2, plus 1.5 mM MgCl$_2$.

After the addition of 0.5M K$_2$CO$_3$, the plates were observed for the yellow color indicative of a positive reaction signifying the presence of anti-IUrd antibody. Quantitation was accomplished photometrically at 415 nm. Positive cells from the fusion wells were then recloned by limiting dilution and then recloned by plating single cells in agarose, and the colonies were transferred to separate flasks or plates.

The ELISA assay was also performed on 96-well microculture plates on which monolayers of a cell line were grown. The cells were grown in a culture medium with or without 10 μM BrdUrd for approximately 24 hours, and then fixed with 70% ethanol. In this case the cells containing bromodeoxyuridine incorporated into their DNA were assayed after denaturing the DNA by treatment with 0.07N NaOH for 2 minutes. The plates were then washed free of the NaOH, and supernatant culture medium was added and the wells treated as described above for the ELISA plates containing IU-BSA.

Those clones of hybridoma cells which produced antibodies that reacted with Iodouridine-SA according to the ELISA technique described above were expanded in tissue culture flasks. In a typical experiment, the culture media from such flasks are preserved by precipitation with saturated ammonium sulfate (final concentration, 50%). The precipitate was dialyzed against phosphate-buffered saline (PBS). The antibody is then purified using conventional procedures, for example by affinity chromatography, or the antibody can be frozen for use as the concentrated culture medium or the antibody can be lyophilized.

A deposit of the mouse hybridoma culture identified herein as B44 is on deposit with the American Type Culture Collection and is assigned the ATCC accession number HB-8150. This cell line is capable of producing anti-BrdUrd antibody. The cell line is conveniently frozen in liquid nitrogen.

The procedures of the present invention need not be limited to cell culture techniques. Another approach to monoclonal antibody production is the injection of the hybridoma cells into a histocompatible, immunocompromised animal, for example, BALB/c mice in the case of hybrids from BALB/c mice and plasmacytoma cells derived from BALB/c mice. An ascites tumor is produced which yields very large amounts of antibody in the serum and ascites fluid of the animal, which is harvested and the antibody isolated using known techniques.

Characterization of the Anti-BrdUrd Monoclonal Antibody Produced by the Hybridoma Cell Line Initial characterization of clones was performed by hapten-inhibition using the ELISA technique described above. Supernatant media from six of the clones were analyzed in detail. Serial dilutions of the culture media were added to microtiter wells together with 50 μg per well of IdUrd. The soluble nucleoside analogue competed with IUrd-BSA for binding to the antibody preparations. On the other hand, thymidine did not compete with the clone B44 antibody, which demonstrated the specificity of that antibody for IdUrd. The results are depicted in FIG. 1. Three of the six clones tested in this manner gave a similar result.

The products of these clones were also tested against BrdUrd-containing cell monolayers by the ELISA method, as described above. Only the B44 clone reacted with BrdUrd-incorporated nuclei, but not with the control, non-substituted nuclei. The supernatants from 24 of 170 clones of the fusion between spleen cells and SP2/O plasmacytoma cells were positive with respect to IU-BSA binding.

One clone, B44, was selected for further cloning in agarose by limiting dilution, and immunological screening with cells. The ability of B44 supernatants to specifically bind to BrdUrd in cellular DNA was tested on plasmacytoma cells. The cells were incubated for two hours in 10 μM BrdUrd +1 μM FdUrd in Dulbecco's Minimal Essential Medium (DMEM, GIBCO), fixed in methanol/acetic acid (3:1), smeared onto microscope slides, air dried and denatured in 0.07N NaOH for two minutes. The slides were then incubated for 60 minutes with various dilutions of a dialyzed 50% (NH$_4$)$_2$SO$_4$ precipitate (20 mg/ml) of the B44 supernatant culture medium from the hybridoma cells. They were washed twice for five minutes, incubated with fluoresceinated goat anti-mouse immunoglobulin (Cappel), diluted 1:40 in phosphate buffered saline (PBS) containing 5% goat serum for 30 minutes, and again washed in PBS. The cells were then observed by epifluorescence optics. Control cells, grown in medium without BrdUrd, and non-replicating regions of nuclei, were almost invisible under fluorescence excitation. Cells engaged in localized synthesis of DNA showed fluorescence only at the sites of BrdUrd incorporation.

Further experiments tested the immunofluorescent staining in a more quantitative manner. WiL2 human lymphoblast cells were incubated for brief periods in BrdUrd-containing medium and stained in suspension as described in Gratzner and Leif, Cytometry 1:385, 1981, the disclosure of which is hereby incorporated by reference. No cytoplasmic fluorescence was observed by fluorescence microscopy. The cells were then analyzed by flow cytometry.

Figure 2A:
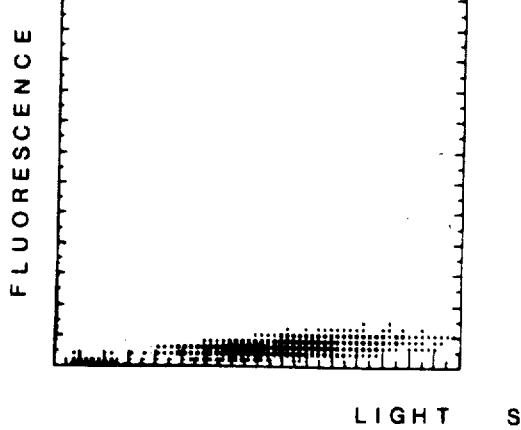
Figure 2B:
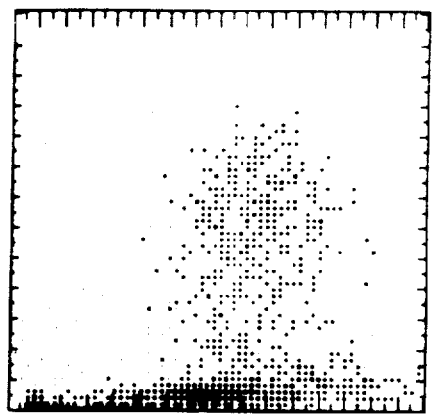

The results of flow cytometric analysis of BrdUrd-labeled WiL2 human lymphoblast cells are shown in FIG. 2. The WiL2 cells were obtained from Dr. William G. Thilly of the Department of Nutrition and Food Science, Massachusetts Institute of Technology. This procedure measured the intensity of fluorescence for each cell and simultaneously the light scatter of each cell. Light scatter is an indication of cell size. In FIG. 2 each dot is a data point representing a number of cells. The dots along the lower portions of FIGS. 2A and 2B represent "noise" and are disregarded.

The cells were pulsed with 10 μM BrdUrd for six minutes, fixed in 70% ethanol and stained in suspension with concentrated (6X) supernatant medium from the B44 cultures according to a method described above. The second antibody was fluoresceinated goat anti-mouse immunoglobulin (Cappel) diluted 1:80 in PBS +5% goat serum. Flow cytometric analysis was carried out using the EPICS IV (Coulter Electronics) Cell Sorter. The laser was tuned to 488 nm, at 65 mW. FIG. 2A shows the cells incubated without BrdUrd; FIG. 2B shows the cells that were incubated in 10 μM BrdUrd. In total 10,000 cells were analyzed.

Pulses of BrdUrd as short as six minutes were sufficient to demonstrate the incorporation of BrdUrd by flow cytometry. Non-BrdUrd-labeled cells exhibited about 10-fold less fluorescence than that of the BrdUrd-labeled cells (FIG. 2). When the cells were stained with the concentrated antibody preparation (20 mg/ml) the fluorescence intensity of non-BrdUrd-labeled cells, as measured by flow cytometry, was increased by less than 1%. This result is in contrast to previous studies using rabbit heteroclonal, anti-BrdUrd serum in which careful titrations were necessary in order to arrive at a serum concentration which specifically stained BrdUrd-labeled cells.

These results indicate that monoclonal antibodies specific for BrdUrd can provide a sensitive method for detecting DNA replication in single cells in a manner analogous to the use of $^3$H-thymidine. The fluorescence intensity per cell has been found to be directly related to the amount of BrdUrd incorporated into the cells. Accordingly fluorescent staining of cells by the monoclonal antibody can be used to estimate the rate of DNA synthesis per cell.

The cells of this invention represent a hybrid culture since: (a) they were selected for growth in HAT medium, where neither the parental spleen cells nor SP2/O plasmacytoma cells can propagate; (b) the cells have been cloned a minimum of four times from colonies which presumably were derived from single cells; (c) the mean DNA content per cell of the hybridoma line analyzed has a higher DNA content than either parental strain, as measured by flow cytometry, strongly suggesting that a new cell line was created by the initial cell fusion; and (d) this hybrid cell line produced an antibody highly specific for 5-Bromodeoxyuridine (BrdUrd) or 5-Iododeoxyuridine (IdUrd) whereas the SP2/O parental cell line does not.

I claim:

1. A hybridoma which is deposited at the American Type Culture Collection under ATCC accession number HB-8150 and which is composed of a hybrid cell resulting from the fusion of a murine plasmacytoma cell from plasmacytoma cell line SP 2/O Ag 15 with an antibody-producing mouse spleen cell from a mouse immunized with the conjugate of 5-bromouridine or 5-iodouridine and an albumin carrier molecule, said cell producing antibodies specific for 5-bromodeoxyuridine or 5-iododeoxyuridine.

* * * * *